US012806010B2

(12) United States Patent
Clapp et al.

(10) Patent No.: US 12,806,010 B2
(45) Date of Patent: Nov. 24, 2026

(54) PROSTHETIC HEART VALVE DEVICE

(71) Applicant: Laguna Tech LLC, Irvine, CA (US)

(72) Inventors: Charles Clapp, Lake Forest, CA (US); Wei Wang, Garden Grove, CA (US); Gilbert Madrid, Dana Point, CA (US)

(73) Assignee: Laguna Tech LLC, Irvine, CA (US)

( * ) Notice: Subject to any disclaimer, the term of this patent is extended or adjusted under 35 U.S.C. 154(b) by 445 days.

(21) Appl. No.: 18/386,207

(22) Filed: Nov. 1, 2023

(65) Prior Publication Data

US 2024/0065832 A1 Feb. 29, 2024

Related U.S. Application Data

(63) Continuation of application No. 17/394,190, filed on Aug. 4, 2021, now Pat. No. 11,806,233.

(51) Int. Cl.
*A61F 2/24* (2006.01)

(52) U.S. Cl.
CPC .......... *A61F 2/2418* (2013.01); *A61F 2/2427* (2013.01); *A61F 2220/0083* (2013.01)

(58) Field of Classification Search
None
See application file for complete search history.

(56) References Cited

U.S. PATENT DOCUMENTS 7,914,575 B2 3/2011 Guyenot et al.
8,002,825 B2 8/2011 Letac et al.
8,398,704 B2 3/2013 Straubinger et al.
8,685,086 B2 * 4/2014 Navia .................. A61F 2/2418 623/2.14
9,615,921 B2 * 4/2017 Alkhatib ............... A61F 2/2412
10,433,954 B2 * 10/2019 Girard .................. A61F 2/2409
(Continued)

FOREIGN PATENT DOCUMENTS

CN 101919752 B 4/2014
CN 105125322 B 3/2017
(Continued)

OTHER PUBLICATIONS

International Preliminary Report in corresponding PCT Appl. No. PCT/US2022/038803.
(Continued)

*Primary Examiner* — Ann Hu
(74) *Attorney, Agent, or Firm* — Raymond Sun

(57) ABSTRACT

The present invention provides a prosthetic heart valve device that has a frame, and a leaflet assembly having a plurality of leaflets that are secured to the frame. The frame is defined by an annular body and has three spaced-apart commissure regions, each commissure region having a commissure post extending from a proximal outflow end of the frame. A first clipping arm and a second clipping arm extend from opposite sides of each commissure post, each clipping arm extending from each commissure post at an obtuse angle with respect to each commissure post. Each clipping arm has a free end with a tip provided at the free end. The body has a first diameter at a location where the tips of the clipping arms are located, and the tips of the clipping arms extend away from define a second diameter, with the second diameter being greater than or equal to the first diameter.

14 Claims, 16 Drawing Sheets

(56) References Cited

U.S. PATENT DOCUMENTS

| | | | | |
|---|---|---|---|---|
| 10,524,904 | B2 * | 1/2020 | O'Connell ............ | A61F 2/2427 |
| 10,639,143 | B2 | 5/2020 | Oba et al. | |
| 10,993,805 | B2 | 5/2021 | Straubinger et al. | |
| 11,259,923 | B2 | 3/2022 | Zhang et al. | |
| 11,337,800 | B2 | 5/2022 | Schreck et al. | |
| 11,357,624 | B2 * | 6/2022 | Guyenot ............... | A61F 2/2418 |
| 11,806,233 | B2 * | 11/2023 | Clapp ................... | A61F 2/2436 |
| 12,226,313 | B2 * | 2/2025 | Clapp ................... | A61F 2/2433 |
| 2005/0137686 | A1 | 6/2005 | Salahieh et al. | |
| 2006/0212111 | A1 * | 9/2006 | Case ..................... | A61F 2/2475 623/1.24 |
| 2007/0288087 | A1 * | 12/2007 | Fearnot ................. | A61F 2/2418 623/2.18 |
| 2009/0216312 | A1 * | 8/2009 | Straubinger .......... | A61F 2/2418 623/1.36 |
| 2010/0049313 | A1 | 2/2010 | Alon et al. | |
| 2010/0191320 | A1 * | 7/2010 | Straubinger .......... | A61F 2/2418 623/1.26 |
| 2010/0249911 | A1 * | 9/2010 | Alkhatib ............... | A61F 2/2418 623/1.26 |
| 2010/0268332 | A1 * | 10/2010 | Tuval .................... | A61F 2/2436 623/2.1 |
| 2011/0208297 | A1 | 8/2011 | Tuval et al. | |
| 2011/0295363 | A1 | 12/2011 | Girard et al. | |
| 2012/0303038 | A1 | 11/2012 | Durante et al. | |
| 2013/0018458 | A1 | 1/2013 | Yohanan et al. | |
| 2013/0310928 | A1 | 11/2013 | Morriss | |
| 2014/0277427 | A1 * | 9/2014 | Ratz ...................... | A61F 2/2409 623/2.38 |
| 2015/0018944 | A1 * | 1/2015 | O'Connell ............ | A61F 2/2427 623/2.42 |
| 2015/0173897 | A1 * | 6/2015 | Raanani ................ | A61F 2/2418 623/2.11 |
| 2015/0351904 | A1 | 12/2015 | Cooper et al. | |
| 2015/0359629 | A1 * | 12/2015 | Ganesan ............... | A61F 2/2409 623/2.14 |
| 2016/0038280 | A1 | 2/2016 | Morriss et al. | |
| 2016/0158003 | A1 * | 6/2016 | Wallace .................... | A61F 2/24 623/2.17 |
| 2016/0213465 | A1 | 7/2016 | Girard et al. | |
| 2016/0354203 | A1 | 12/2016 | Tuval | |
| 2017/0128199 | A1 | 5/2017 | Gurovich et al. | |
| 2017/0209265 | A1 * | 7/2017 | Karapetian ............. | A61F 2/246 |
| 2017/0216023 | A1 | 8/2017 | Lane et al. | |
| 2018/0177595 | A1 | 6/2018 | Krans et al. | |
| 2018/0221147 | A1 | 8/2018 | Ganesan et al. | |
| 2018/0303612 | A1 * | 10/2018 | Pasquino .............. | A61F 2/2418 |
| 2019/0151091 | A1 | 5/2019 | Dwork et al. | |
| 2019/0224008 | A1 | 7/2019 | Bressloff et al. | |
| 2020/0060818 | A1 | 2/2020 | Geist | |
| 2020/0197172 | A1 | 6/2020 | Tuval et al. | |
| 2021/0077083 | A1 | 3/2021 | Thambar et al. | |
| 2021/0145576 | A1 | 5/2021 | Becerra et al. | |
| 2021/0154010 | A1 | 5/2021 | Schneider et al. | |
| 2022/0008198 | A1 | 1/2022 | Dai | |
| 2022/0015898 | A1 | 1/2022 | Li et al. | |
| 2023/0038809 | A1 | 2/2023 | Clapp et al. | |

FOREIGN PATENT DOCUMENTS

| | | | | |
|---|---|---|---|---|
| CN | 105662652 | B | 12/2017 | |
| CN | 110507451 | A | 11/2019 | |
| CN | 112618105 | A | 4/2021 | |
| CN | 114886614 | A | 8/2022 | |
| CN | 114886615 | A | 8/2022 | |
| EP | 3583920 | A1 | 12/2019 | |
| WO | WO-2010086460 | A1 * | 8/2010 | ........... A61F 2/2418 |
| WO | WO2010/117680 | A1 | 10/2010 | |
| WO | WO2013/012801 | A2 | 1/2013 | |
| WO | WO2014/153152 | A1 | 9/2014 | |
| WO | WO2019/136292 | A1 | 7/2019 | |
| WO | WO-2021202172 | A1 * | 10/2021 | ........... A61F 2/2418 |
| WO | WO-2022010958 | A1 * | 1/2022 | ........... A61F 2/2418 |
| WO | WO2023/012680 | A1 | 2/2023 | |
| WO | WO2023/014593 | A1 | 2/2023 | |

OTHER PUBLICATIONS

PCT International Search Report and Written Opinion for PCT/IB2022/059766, Laguna Tech USA, Inc., Forms PCT/ISA/220, 210, and 237 dated Mar. 15, 2023 (17 pages).

* cited by examiner

PROSTHETIC HEART VALVE DEVICE

BACKGROUND OF THE INVENTION

1. Field of the Invention

The present invention relates to a prosthetic heart valve device, and in particular, to a prosthetic heart valve for use in treating aortic valve insufficiency.

2. Description of the Prior Art

Aortic valve insufficiency (AI), also known as aortic regurgitation (AR), is a serious and potentially fatal structural heart disease afflicting millions of patients worldwide. AI is characterized by volume overload and eccentric hypertrophy associated with left ventricular (LV) cavity structural modifications and progressive dysfunction. This results in the dilatation of the aortic root/annulus, which leads to aortic regurgitation. Left untreated, this disease can become progressively worse and may eventually lead to patient death.

To-date, there are only two known minimally invasive transcatheter aortic valve implantation devices for treating AI disease. The first device is manufactured by JenaValve, and utilizes a frame design with "feeler" arches, to align with the native anatomy, and to clip the native valve leaflets during deployment. However, the JenaValve design is difficult to deliver and deploy due to its open cell design, and does not have any structure to prevent native leaflet interaction with the prosthetic leaflets. The JenaValve device also has a significant asymmetric construction that includes different cell sizes, and a notched design for leaflet attachment. All these features make the device crimping very challenging, and thus the deployment can be difficult to control.

The second device is manufactured by JC Medical, and utilizes a two-piece design, which has U-shaped anchor rings that are deployed in the native cusps, followed by the self-expanding valve endoprosthesis. The two separate pieces are anchored together utilizing suture/wire, which allow for the potential to fail during or after implantation, potentially causing migration and/or device embolization. The major disadvantage of this device is a metal-on-metal design that can increase the profile and affect the long-term durability of the valve.

The transcatheter aortic valve implantation devices for treating AI disease are to be contrasted with traditional transcatheter valve designs, which are indicated for the treatment of aortic stenosis. The traditional stenotic valve provides a secure ring to deploy and anchor a native valve. However, in a pure AI disease state, there is not a secure ring to anchor inside. Therefore, utilizing the native anatomy to anchor the valve is more difficult in non-stenotic valves that are used to treat AI.

Thus, there remains a need for a prosthetic heart valve that can be used to treat AI, and which overcomes the deficiencies of the existing devices.

SUMMARY OF THE DISCLOSURE

The present invention provides a prosthetic heart valve that can be used effectively to treat AI while avoiding the drawbacks experienced by the known devices.

In order to accomplish the objects of the present invention, the present invention provides a prosthetic heart valve device that has a frame, and a leaflet assembly having a plurality of leaflets that are secured to the frame. The frame is defined by an annular body that is defined by an arrangement of cells. The frame has three spaced-apart commissure regions, each commissure region having a commissure post extending from a proximal outflow end of the frame. A first clipping arm and a second clipping arm extend from opposite sides of each commissure post, each clipping arm extending from each commissure post at an angle that ranges from 90 to 180 degrees with respect to each commissure post. Each clipping arm has a free end with a tip provided at the free end. The body has a first diameter at a location where the tips of the clipping arms are located, and the tips of the clipping arms extend away from define a second diameter, with the second diameter being greater than or equal to the first diameter.

The present invention also provides a method of securing the prosthetic heart valve device at an aortic annulus that includes a plurality of native leaflets. This method includes the steps of crimping the heart valve device inside a delivery system, delivering the heart valve device to the annulus, and deploying the heart valve device at the annulus with at least some of the native leaflets positioned between the clipping arms and the body.

According to another embodiment, some of the native leaflets can also be positioned around an external surface of some of the clipping arms.

The method of the present invention can also include the steps of:

- advancing the delivery system through the aortic arch and the ascending aorta of the patient with a distal portion of the delivery system passing through the aortic annulus into the ventricle;
- retracting a portion of the delivery system so that the clipping arms are exposed in the ventricle;
- retracting the delivery system and the heart valve device so that the clipping arms have completely cleared the aortic annulus and are now positioned inside the aortic root;
- with distal ends of the clipping arms positioned above the native aortic valve, advancing the heart valve device distally until the clipping arms drop into the cusps of the native leaflets; and
- retracting the remainder of the delivery system to deploy the body of the frame at the aortic annulus.

The present invention provides a prosthetic heart valve device, and a method of deployment thereof, that can be effectively deployed at an aortic annulus in a manner which minimizes post-deployment shifting or movement of the deployed heart valve device.

BRIEF DESCRIPTION OF THE DRAWINGS

FIG. 100 illustrates the various components of the delivery system of FIG. 10A shown in the fully deployed configuration, with the device of FIG. 5 compressed on the inner tube.

DETAILED DESCRIPTION OF THE PREFERRED EMBODIMENTS

Figure 2:
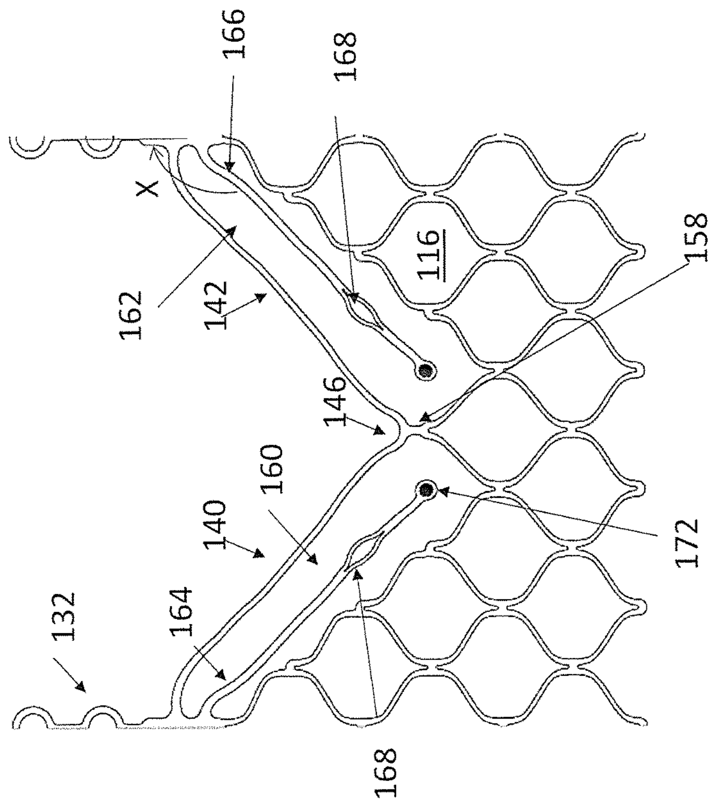
FIG. 2 is a flattened view of a portion of the frame of FIG. 1.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

FIGS. 1-9 illustrate a prosthetic heart valve device 100 according to the present invention. The device 100 has a frame 110 that is defined by an annular body 112 that includes three commissure regions 114. The body 112 is defined by an arrangement of cells 116. Each cell 116 can be defined by four struts 118 to form any desired shape. FIGS. 1-9 show the struts 118 being curved to form a tear-drop shaped cell, although any other configuration (e.g., four straight struts to form a diamond-shaped cell) can also be employed.

Referring first to FIGS. 1-4, the body 112 can be configured with three cell regions 120*a*, 120*b* and 120*c* that form an annular band. Each cell region 120*a*, 120*b* and 120*c* consists of cells, having a first row 122 of cells 116, a second row 124 of cells 116, a third row 126 of cells 116, a fourth row 128 of cells 116 and a fifth row 130 of cells 116. The first row 122 defines the distal (or inflow) end of the frame 110 and has the largest number (e.g., five in this embodiment) of cells 116. The second row 124 is immediately proximal of, and staggered from, the first row 122 and the same or next largest number (e.g., four in this embodiment) of cells 116. The third row 126 is immediately proximal of, and staggered from, the second row 124 and the next largest number (e.g., three in this embodiment) of cells 116. The fourth row 128 is immediately proximal of, and staggered from, the third row 126 and the next largest number (e.g., two in this embodiment) of cells 116. The fifth row 130 is immediately proximal of, and staggered from, the fourth row 128 and the smallest number (e.g., one in this embodiment) of cells 116. The fifth row 130 is also the proximal-most (outflow) row of cells 116, and each cell 116 in the fifth row 130 support a respective commissure post 132.

Figure 1:
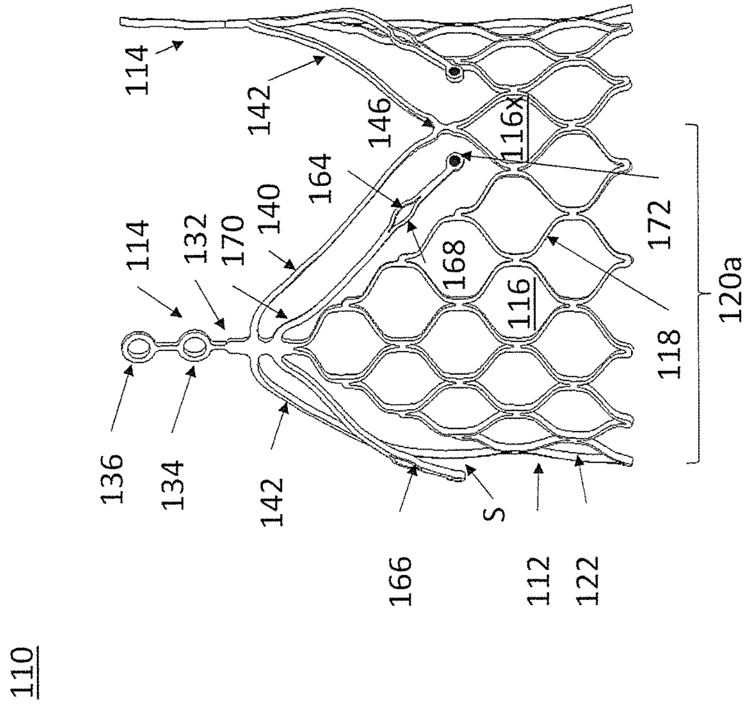
FIG. 1 is a side perspective view of the frame of a prosthetic heart valve device according to a first embodiment of the present invention.

As best shown in FIG. 1, the distal (inflow) end of the body 112 can be slightly flared so that the increased diameter at the distal (inflow) end can be used to better secure the frame 110 at the native annulus. In particular, the cells 116 in the first row 122 can be shape-set to be flared and define a larger diameter than the next row 124 of cells 116.

Each commissure region 114 includes a connection portion, and in this embodiment, the connection portion is configured as a commissure post 132 extending from the distal-most row of cells 116. Each commissure post 132 includes at least one eyelet 134 that extends from the top (proximal end) of the post 132, and in this embodiment, there is also a second eyelet 136. In case where a plurality of eyelets 136 is provided, the plurality of eyelets 136 can be arranged along the length of the respective commissure post 132, although other arrangements can also be employed.

Figure 3:
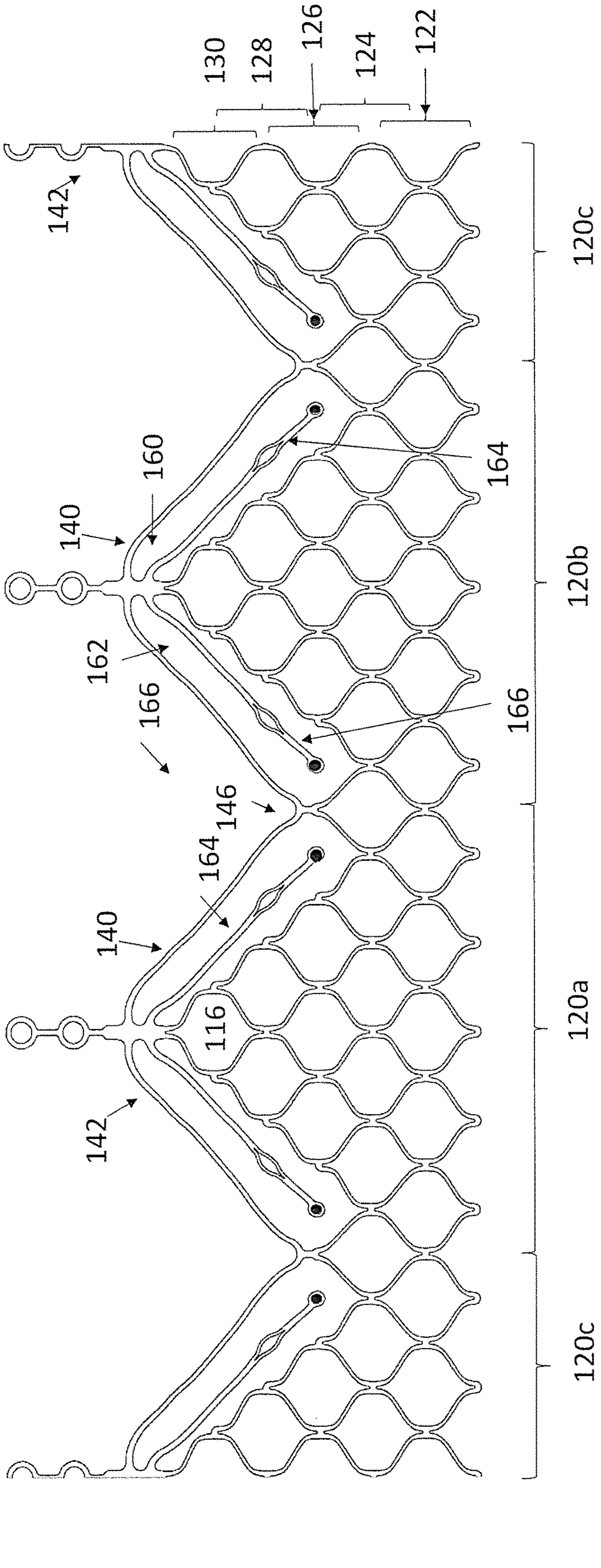
FIG. 3 is a flattened view of the entire frame of FIG. 1.

A first frame arm 140 and a second frame arm 142 extend from opposite sides of each post 132. Each first arm 140 from one post 132 is connected at a distal-facing apex 146 with the second arm 142 from an adjacent post 132. Each apex 146 is joined or connected at a joint 158 with an apex of a cell 116*x* in row 124. Each arm 140 and 142 can be straight or wavy (as shown, with different curved regions along the arm) or curved. The first frame arm 140 is connected with the frame 110 at a joint that is closer to the distal (or inflow) end than the eyelet 134. Each arm 140 and 142 is formed as a single rod or deformable mesh band. As shown in FIG. 3, the angle between each arm 140 and 142 and the axis of the frame ranges from 30 degrees to 85 degrees.

In addition, a first angled space 160 is defined by each first arm 140 and the corresponding cell region 120*a*, 120*b* or 120*c*, and a second angled space 162 is defined by each second arm 142 and the corresponding cell region 120*a*, 120*b* or 120*c*. The first angled space 160 is inclined towards the distal (or inflow) end away from the corresponding post 132. The first arm 140 and the second arm 142 generally form a V-shape between two adjacent posts 132, and the first arm 140 and the second arm 142 can be symmetrically disposed at opposite sides of the imaginary apex of the V-shape.

A first clipping arm 164 and a second clipping arm 166 extend from opposite sides of each connection portion for connecting the clipping arms 164, 166 and the frame (i.e., here it would be the posts 132) from a location between the first arm 140 and the second arm 142, respectively, and the corresponding distal-most row of cells 116. Alternatively, the first clipping arm 164 and the second clipping arm 166 can extend from opposite sides of the same row of cells 116. Preferably, the circumferential span between the first clipping arm 164 and the second clipping arm 166 is small. More preferably, the axial span between the first clipping arm 164 and the second clipping arm 166 is also small. In the present embodiment, the joint of the first clipping arm 164 with the corresponding post is adjacent to the joint of the second clipping arm 166 with the same corresponding post. Preferably, the first clipping arm 164 and the second clipping arm 166 can be symmetrically arranged at opposite sides of the corresponding post 132. The joint of the first arm 140 and the corresponding post is closer to the proximal (or outflow) end than the joint of the first clipping arm 164 and the second clipping arm 166. In other embodiments, additional clipping arms 164, 166 can be provided on any post 132, in which case all the clipping arms 164, 166 on the same side of the post 132 can be considered as being of one group of clipping arms. The ends of the clipping arms in one group for connecting with the post can be joined at the same position or adjacent to each other, and the free ends of the clipping arms in one group can be connected together. In some embodiments, each clipping arm can be formed as a deformable mesh band.

The first angled space 160 can be considered as a hollowed area of the frame 110. Before the clipping arms 164 and 166 are released and expanded, the clipping arms 164 and 166 can be located within the respective hollowed areas, which avoids providing the frame 100 with a large outer diameter by avoiding a radial overlap during loading of the device 100. Each clipping arm 164, 166 defines an angle X between the respective clipping arm 164, 166 and the respective commissure post 132. See FIG. 2. This angle X ranges from 90 degrees to 180 degrees, and is preferably about 120 degrees. The clipping arms 164 and 166 function as beams, so the term "beam" is also used interchangeably herein with the term "clipping arm", and are intended to have the same meanings. Each clipping arm 164 and 166 can include one or more slots 168 within the body of the arm 164 or 166, and each arm 164 and 166 has a first end 170 connected to the corresponding post 132, and a second end having an eyelet 172 that slightly enlarges the second end. Each first clipping arm 164 and second clipping arm 166 extends into the vicinity of the first angled space 160 and the second angled space 162, respectively, and functions to clip a portion of a native valve leaflet (see FIGS. 8 and 9) against the body 112. The clipping arms 164, 166 can be provided in one piece, cut from the same tubular structure as the body 112, or attached after cutting by various methods, such as suture attachment or laser welding.

Each slot 168 can be an open space in the body of the arm 164 or 166, and this open space can have any desired shape, including diamond shaped (as shown). As such, these slots 168 can be considered to be extender cells. The purpose of these extender cells 168 is to lengthen the arm 164 or 166 after the initial frame cutting. The extender cells 168 are designed in such a way that, prior to shape set, they are in the open configuration (i.e., struts are further apart) but after shape-set, they are in the closed configuration. By changing from the open to the closed configuration, the extender cells 168 foreshorten and cause the beams to elongate. This allows the frame 110 to be designed out of a single tubing and achieve the length required to allow the heart valve device 100 to sit high enough in the aortic annulus to minimize protrusion into the left ventricular outflow tract (LVOT) and thereby minimize risk of conduction system disturbance. Each arm 164 and 166 can have a plurality of extender cells 168 that are spaced-apart along the length of each arm 164, 166. As another alternative, the size of the slots 168 can be varied depending on use, application, and clinical requirements.

Each clipping arm 164 and 166 can have a length of about 18 mm, although the length could be adjusted based on clinical requirements. As shown in the drawings, each arm 164 and 166 extends across most of the respective space 160 and 162. The arms 164 and 166 serve two purposes. First, each arm sits behind the native leaflet, and holds the native leaflet between the arm and the frame body. This allows the native leaflet to be used to improve in the sealing between the native anatomy and prosthesis. Additionally, a secondary clipping mechanism can be obtained by capturing the leaflet between adjacent arms. Second, the arms limit protrusion into the LVOT and thus minimize conduction system impact. The arms 164, 166 are deployed first and are placed such that the tips 172 seat inside the cusp. The tip location can be modulated by changing the length or angle of the arm 164, 166 with the commissure post. Thus, the tip 172 can be designed to be in the optimal location in relation to the inflow of the heart valve, approximately 4-8 mm from the distal most end of the frame 110, thereby limiting protrusion into the LVOT. In addition, the stiffness of the arms 164, 166 can be modulated by changing the thickness of the arms 164, 166 such that there is more or less flexing when contacting the native leaflet. The desired embodiment will seat the valve prosthesis within the native anatomy such that the protrusion of the frame 110 into the LVOT is minimized and reduces instances of PPI (permanent pacemaker implantation). For improved safety, the tips 172 can be provided as a rounded structure and/or covered with a protective layer which is preferably made of a biocompatible synthetic material or biomaterial.

The arms 164, 166 in the current embodiment are shape-set to a larger diameter than the body 112 of the frame 110 by approximately 4 mm. In other words, the outer diameter formed by tracing the tips 172 of all the arms 164, 166 can be equal to or larger than the outer diameter of the body 112 at the circumference location of the tips 172. This can be shown or represented by the space S in FIG. 1. This shape-setting configuration (in addition to the arms 164, 166 being free at one end) allows the arms 164, 166 to expand to a larger diameter during delivery. The larger diameter expansion increases the chances of capturing the native leaflets between the arms 164, 166 and the body 112 of the frame 110, thus increasing the likelihood of correct anatomical placement of the prosthetic device 100. As a non-limiting alternative, each clipping arm 164 and 166 can extend outwardly in a wavy pattern to further improve the clipping effect of the arm to the portion of the native valve leaflet against the body 112 without affecting the positioning in the human body.

An alternative is to provide varying spacing S of the tips 172 along the circumference of the frame 112. For example, the spacing S can be 4 mm at some tips 172, and 3 mm at other tips 172.

The frame 110 can be made of Nitinol or any other known self-expandable material having superelastic memory characteristics.

Even though the frame 110 is described hereinabove with specific reference to one specific embodiment, this is not intended to be limiting and it is also possible to configure the frame 110 differently.

Figure 5:
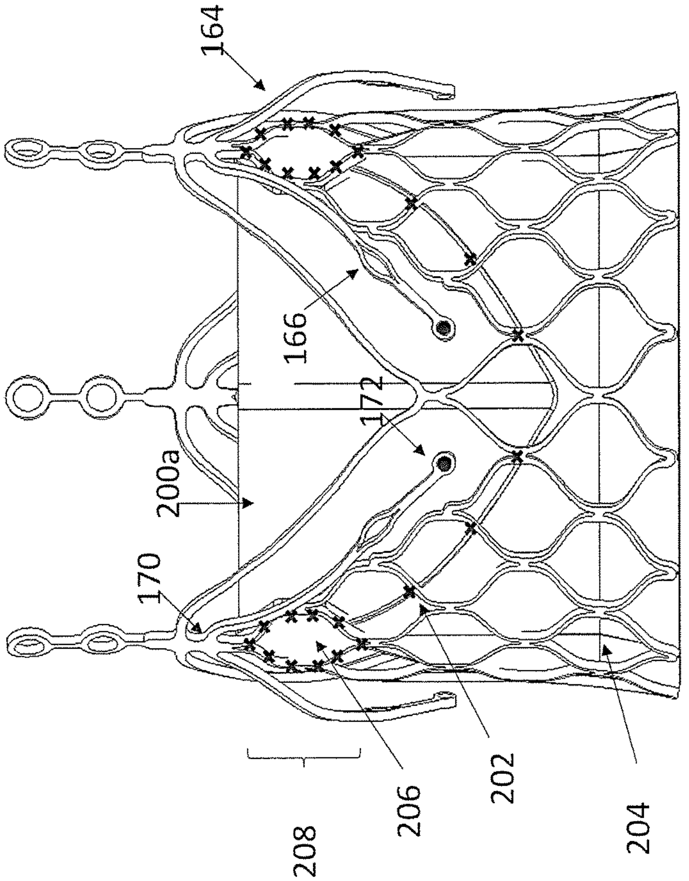
FIG. 5 is a side perspective view of the prosthetic heart valve device according to the first embodiment of the present invention.
Figure 4:
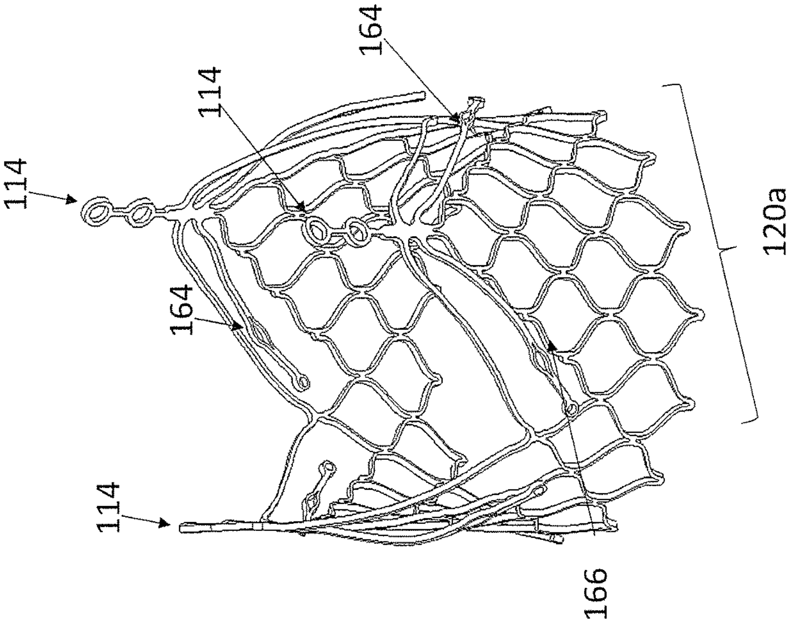
FIG. 4 is a top perspective view of the frame of FIG. 1.
Figure 7:
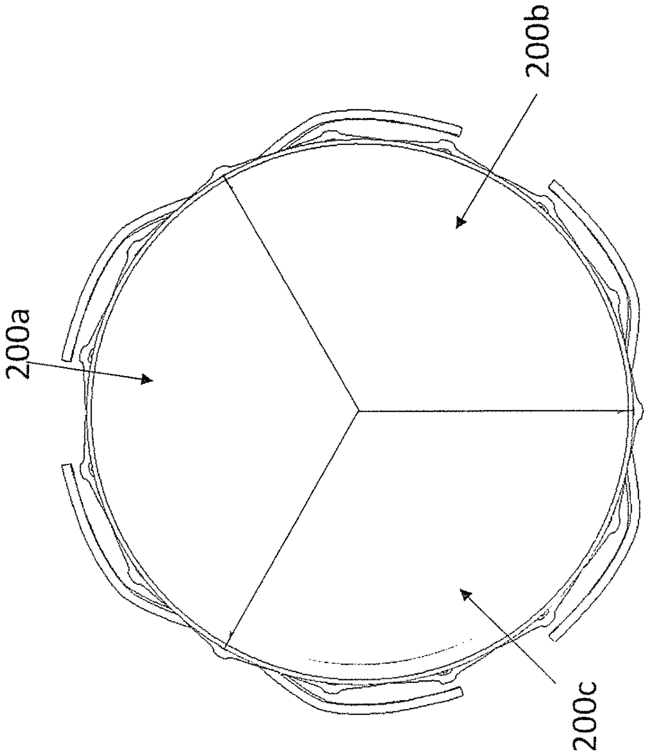
FIG. 7 is a top view of the device of FIG. 5.
Figure 6:
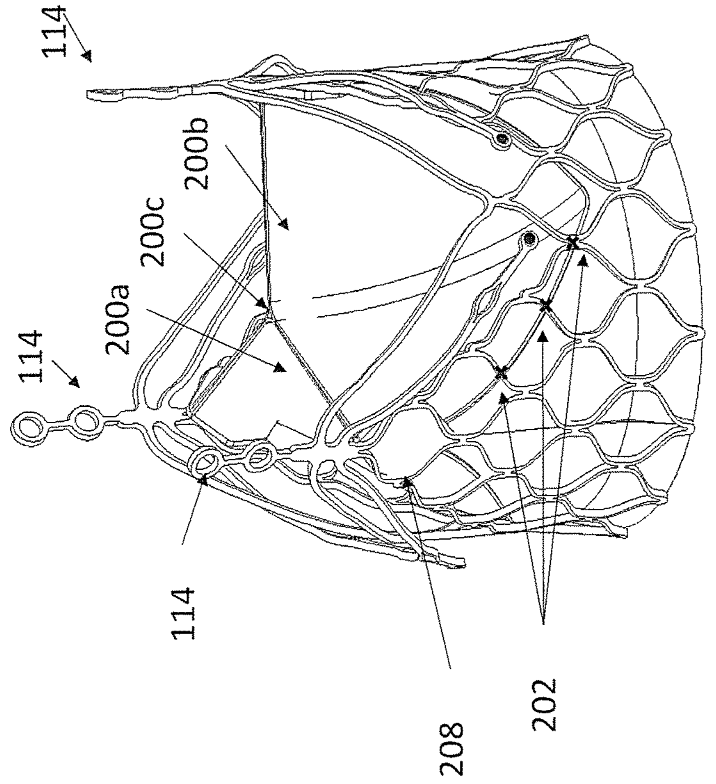
FIG. 6 is a top perspective view of the device of FIG. 5.

Referring now to FIGS. 5-7, the device 100 also has a set of prosthetic leaflets 200*a*, 200*b* and 200*c* that are configured as a conventional tricuspid (three-leaflet) valve. The leaflets 200*a*, 200*b* and 200*c* can be provided in any known desired prosthetic material, including a processed animal tissue such as porcine tissue and bovine tissue, or a synthetic material.

The three leaflets are attached together using a stitch line, and commissure tabs 206 are created by folding back the leaflet tabs and attaching to a cloth material. Commissure tab cloth material can be made from synthetic material (e.g., polyester) and aids in suture retention in attaching the tissue subassembly to the frame 110. Once formed, the leaflet subassembly is stitched to a skirt material 204. The skirt is similarly created from three separate components and stitched together. The skirt material 204 can be made from porcine or bovine tissue, or a synthetic material. Once this sub-assembly is created, the commissure tabs 206 are attached at locations 208 to the frame 110 at the proximal-most row (row 130) of cells 116 to form the commissure. In one embodiment, the seam line between each leaflet 200*a*, 200*b*, 200*c* and skirt material 204 is attached to the frame 110 using stitches (see attachment points 202) at the appropriate locations, although other attachment methods are also possible. Further, additional stitching is utilized to secure the skirt material to the frame 110 between the bottom of the frame 110 and leaflet attachment. An example of attachment points 202 are the points or locations where the leaflet edges are attached to the cells 116. The cells 116 in the row 130 will be utilized for commissure attachment, and the leaflets will be attached along a curved path following the shape of the leaflet through the plurality of cells shown in FIG. 6 as defined by the attachment points 202. The skirt material 204 is attached spanning the space from the leaflet attachment to the bottom of the frame.

The device 100 of the present invention provides a number of benefits over the existing transcatheter aortic valve implantation devices that are used for treating AI disease.

First, the frame 110 has a plurality of beams or clipping arms 164 and 166 that function as cantilever beam-like structures that are designed to clasp onto the native aortic leaflets securely, and to do so with ease. Specifically, during device implantation, the clipping arms 164, 166 are exposed from the delivery catheter first, and are positioned behind and/or around the native leaflets. Once the device 100 is fully deployed, the clipping arms 164, 166 will mechanically clasp onto the native leaflets, thus helping to prevent shifting or movement of the device 100. The mechanical clasp force can be enhanced by shape-setting the clipping arms in a configuration so that the clipping arms are offset to act like clips.

Unlike the existing JenaValve or J-Valve devices, which position three large parabolic or "U" shaped arches behind the three native leaflets, the device 100 of the present invention uses six cantilever beams 164, 166 to clip onto the native leaflets. This provides two major benefits. First, the additional clipping arms or beams increase the likelihood of successfully capturing one or more native leaflets, thus making the procedure easier and safer. Second, successful clasping of the native leaflets can be accomplished in multiple ways, thus making the capture mechanism more reliable. For example, the leaflet clasping can either be obtained by placing all arms 164, 166 behind the native leaflet and securing the native leaflet between the arms 164, 166 and the body 112; or alternatively by placing a plurality of arms 164, 166 behind the native leaflet and a plurality of arms 164, 166 in front of the native leaflet, thus clasping the native leaflet between adjacent arms 164, 166. The underlying benefit of having closely located clipping arms is that they are designed so that they can act as clips with respect to leaflet backing if all the arms 164, 166 are behind the native leaflets. In certain scenarios when some of the arms 164, 166 are not behind the native leaflets, the offset shape-setting has the closely located arm also clasp the native leaflet and provide better anchoring. For example, there can be a clinical situation where multiple clipping arms 164, 166 can be in front of the native leaflets. This positioning of the clipping arms in the front and the back of the native leaflets provides a better clasping action on the native leaflets compared to the existing devices, where the arches of those devices must be positioned behind the native leaflets.

Second, the clipping arms 164, 166 also feature an atraumatic tip (the eyelet 172), which can be loaded with a radiopaque marker 212 for ease of visualization during implantation. There can also be an additional radiopaque marker 214 (see FIG. 16) located in the commissure regions 114 to allow for the comparison of movement between the eyelets 172 and the commissures. Based on the motion of the markers 212, 214 during deployment, these markers can assist in identifying which clipping arm is behind the leaflet and which clipping arm is in front of the leaflet. For example, the marker that is moving at the rhythm of the heartbeat generally can help illustrate that it is touching the nadir of the native leaflets. By having radiopaque markers on the clipping arms and commissure regions, the physician can easily ascertain that the clipping arms are located behind the native leaflets before full deployment of the device 100. This would make the procedure faster and safer.

Third, the frame 110 provides leaflet restraints or leaflet backing, which are long struts (i.e., the arms 140 and 142) emanating from the posts 132. These leaflet-restraint structures provide additional clasping of the native leaflets to the frame 110 while keeping the native leaflet trapped between the clipping arms 164, 166. These leaflet-restraint structures prevent the native leaflets from interfering with the prosthetic leaflets, and can also work with the clipping arms to clip onto the native leaflets.

Fourth, the frame 110 provides a closed cell design, which means that all struts 118 are connected to each other. Such a design allows for the device 100 to be re-sheathed as there are no open cells which would inhibit the catheter sheath from recovering the entirety of the frame 110 due to any struts from open cells catching the outer sheath 306.

Figure 9:
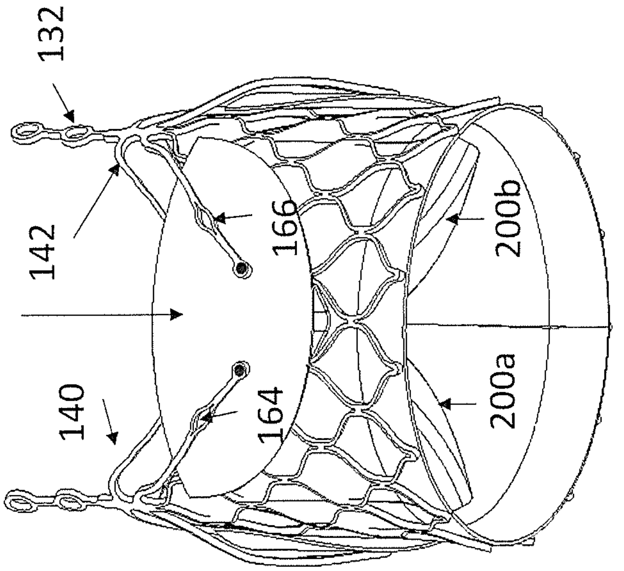
FIG. 9 is a bottom perspective view showing the device of FIG. 5 clipping a native valve leaflet.
Figure 8:
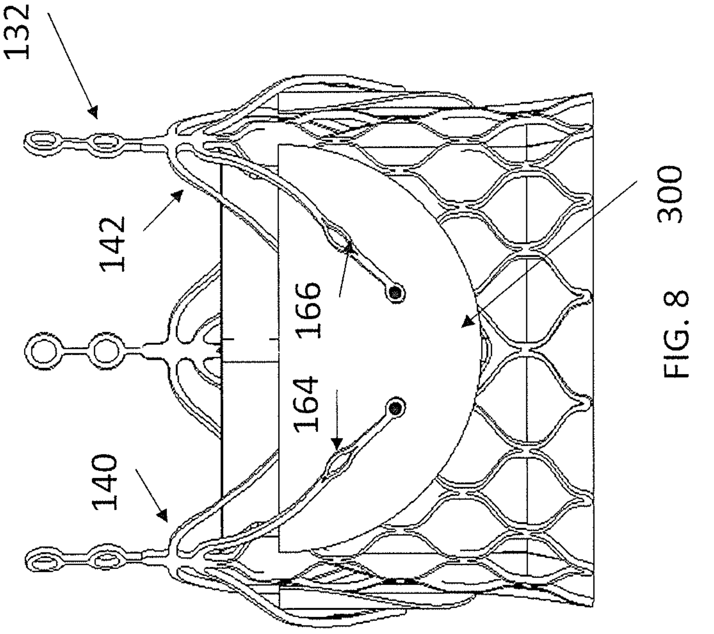
FIG. 8 is a side perspective view showing the device of FIG. 5 clipping a native valve leaflet.

FIGS. 8-11G illustrate how the device 100 is delivered to an aortic annulus and deployed at the aortic annulus. First, FIGS. 8 and 9 show native leaflets 300 clipped or sandwiched between the clipping arms 164, 166 and the body 112 of the frame 110 after the device 100 has been deployed at the aortic annulus.

Figure 10A:
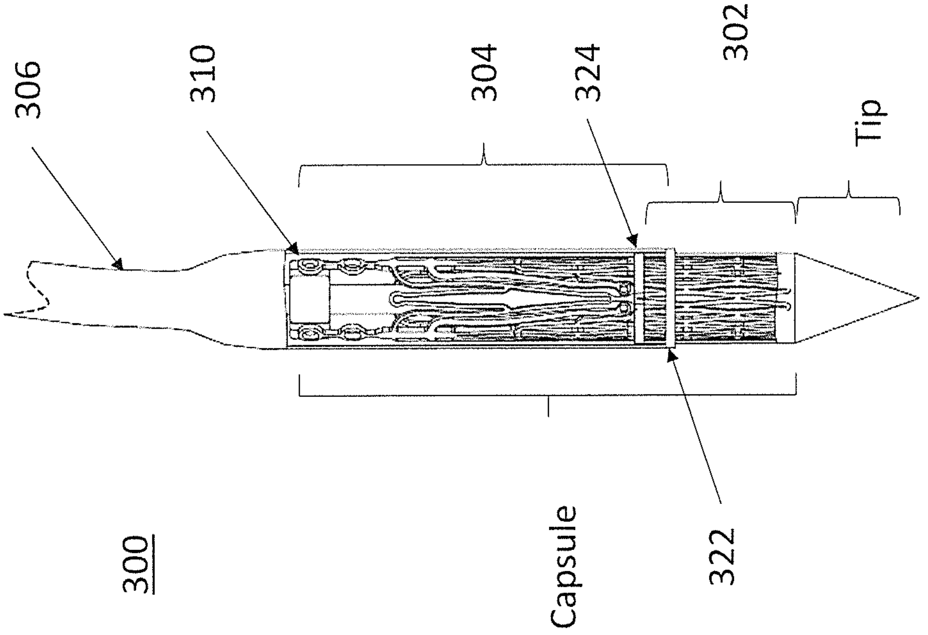
FIG. 10A illustrates the device of FIG. 5 retained in a compressed configuration inside a delivery system.
Figure 10C:
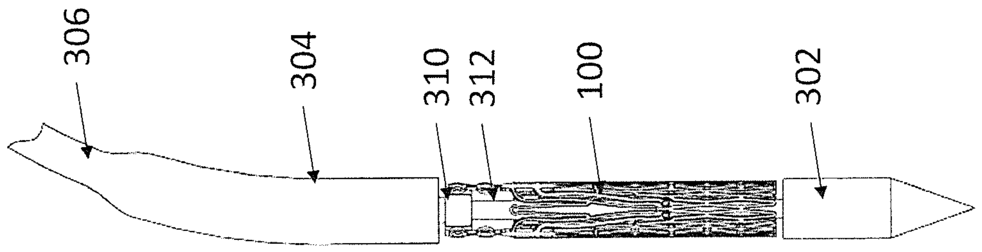
FIG. 10B illustrates the various components of the delivery system of FIG. 10A shown in the fully deployed configuration, without the device of FIG. 5.
Figure 10B:
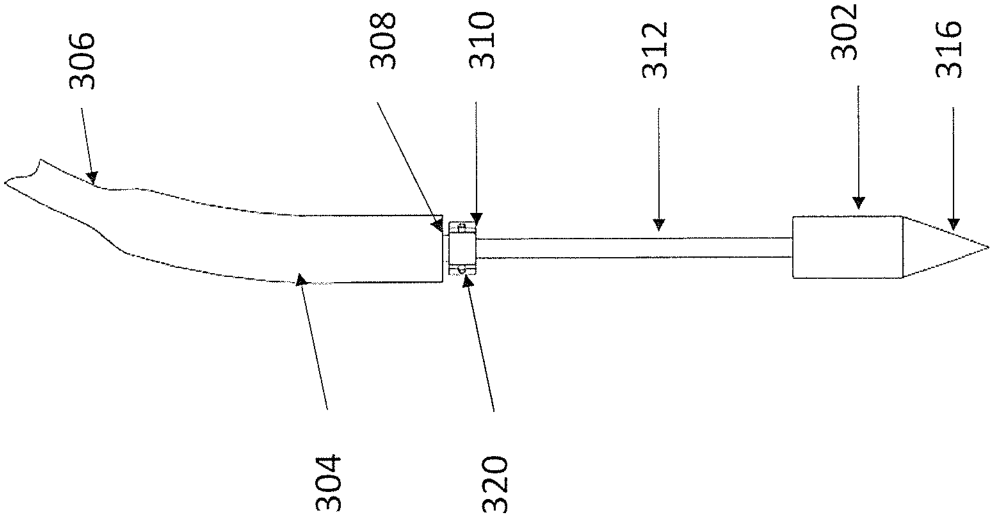

Referring now to FIGS. 10 and 11A-11G, the device 100 is first compressed and held in a delivery system 300. The delivery system 300 shown in FIG. 10 is simply one non-limiting example, and it has an outer sheath 306, an inner tube 308 with a dock 310 at its distal end, a distal sheath 302, and distal tip 316, that are mounted at the distal end of a shaft 312, and a proximal sheath 304. The proximal sheath 304 is mounted at the distal end of the outer sheath 306, and the inner tube 308 extends inside the lumen of the outer sheath 306. The dock 310 has protrusions 320 that are adapted to be clipped inside the eyelets 134/136 to hold or retain the frame 110 inside the delivery system 300. The shaft 312 is slidably retained inside the bore of the inner tube 308.

When the device 100 is crimped or compressed inside the delivery system 300 (see FIGS. 10A and 10C), the commissures 114 are adjacent to the dock 310 with the eyelets 134/136 coupled to the protrusions 320. The compressed device 100 surrounds the shaft 312, with the proximal sheath 304 covering most of the length of the device 100. The distal sheath 302 covers a small length of the distal end of the device 100, with the distal end of the proximal sheath 304 overlapping and covering the proximal end of the distal sheath 302. In particular, the proximal sheath 304 can have a band 322 at its distal-most end, and the distal sheath 302 can have a band 324 at its proximal-most end. The bands 322 and 324 can contain a radiopaque marker to allow for visualization by the clinician during the deployment procedure. The device 100 is contained in its entirety inside a capsule defined by the distal sheath 302 and the proximal sheath 304.

Figure 11B:
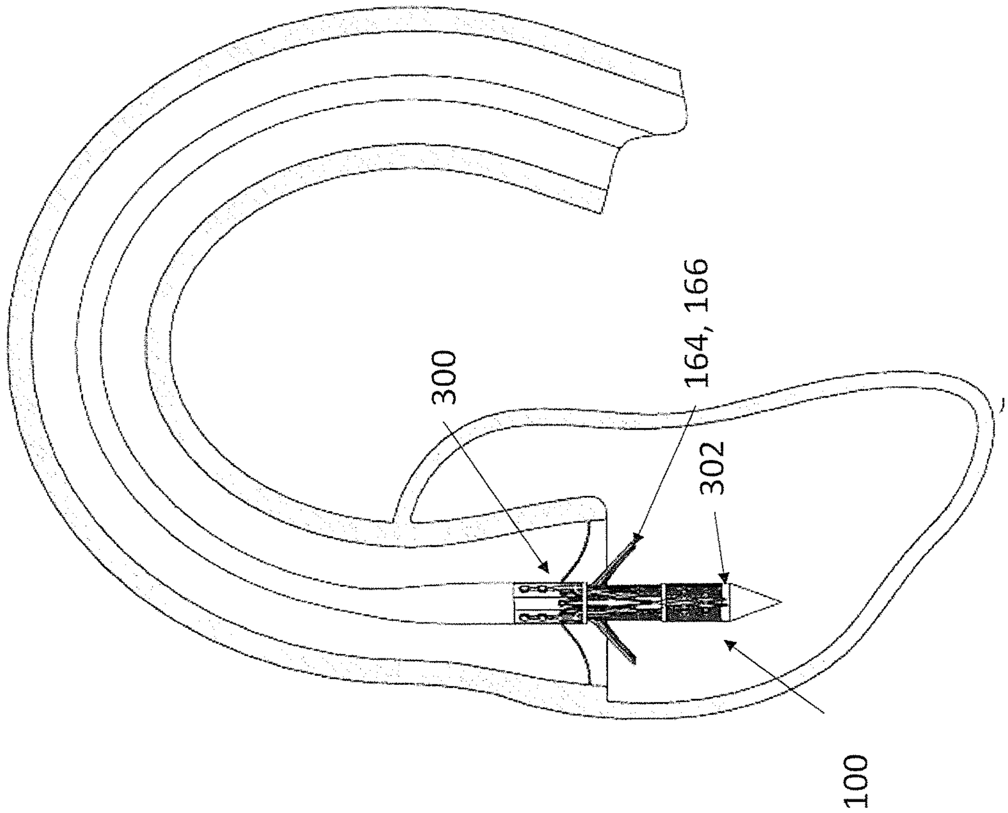
FIGS. 11A-11G illustrate how the device of FIG. 5 is delivered to an aortic annulus of a patient's heart and deployed at the aortic annulus.
Figure 11A:
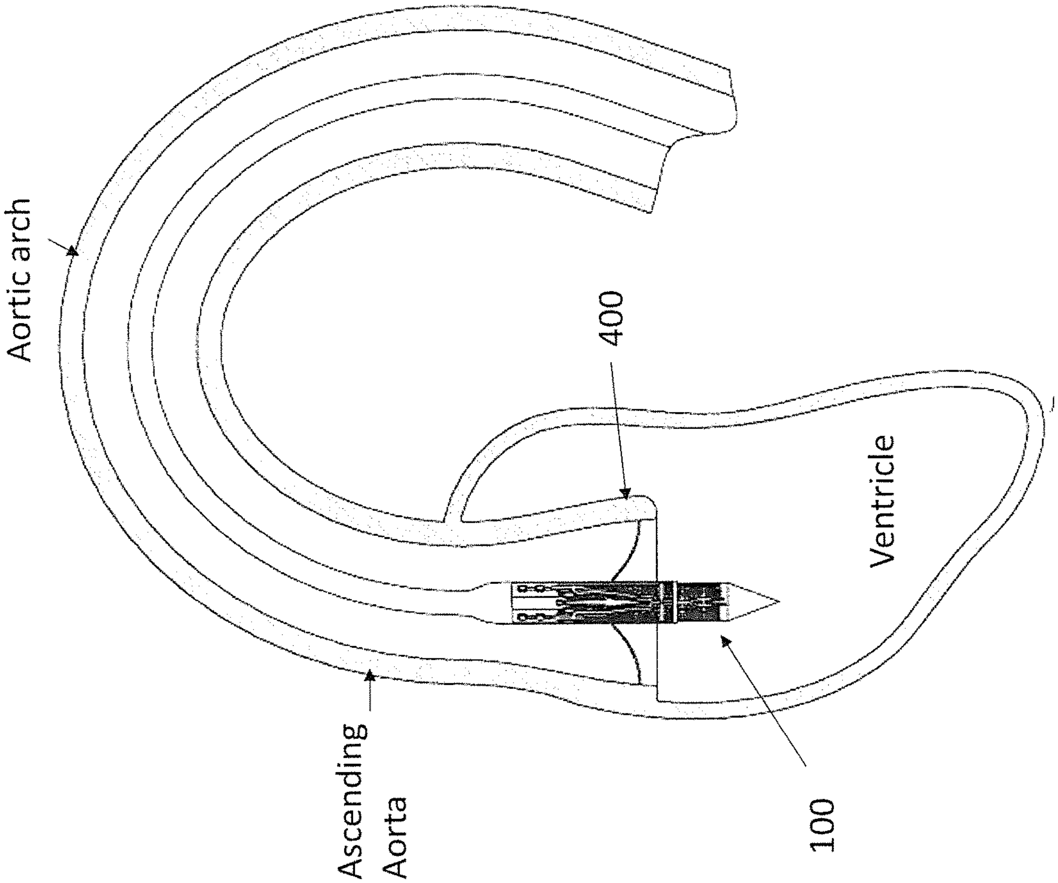
Figure 11D:
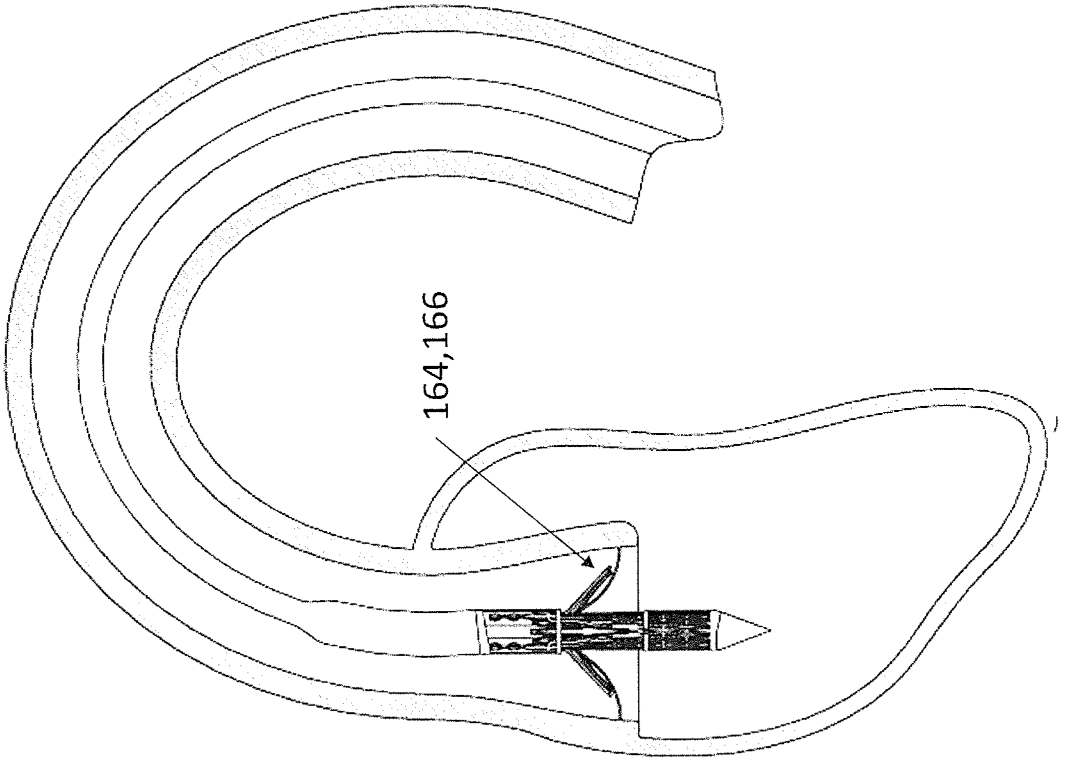
Figure 11C:
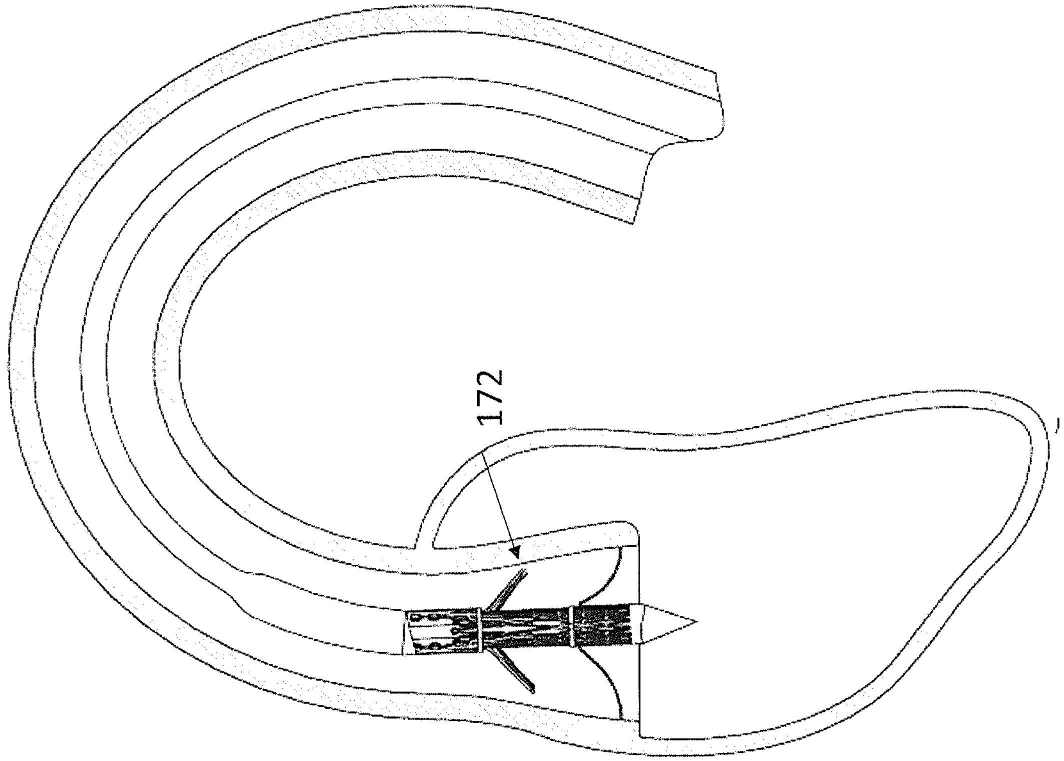
Figure 11F:
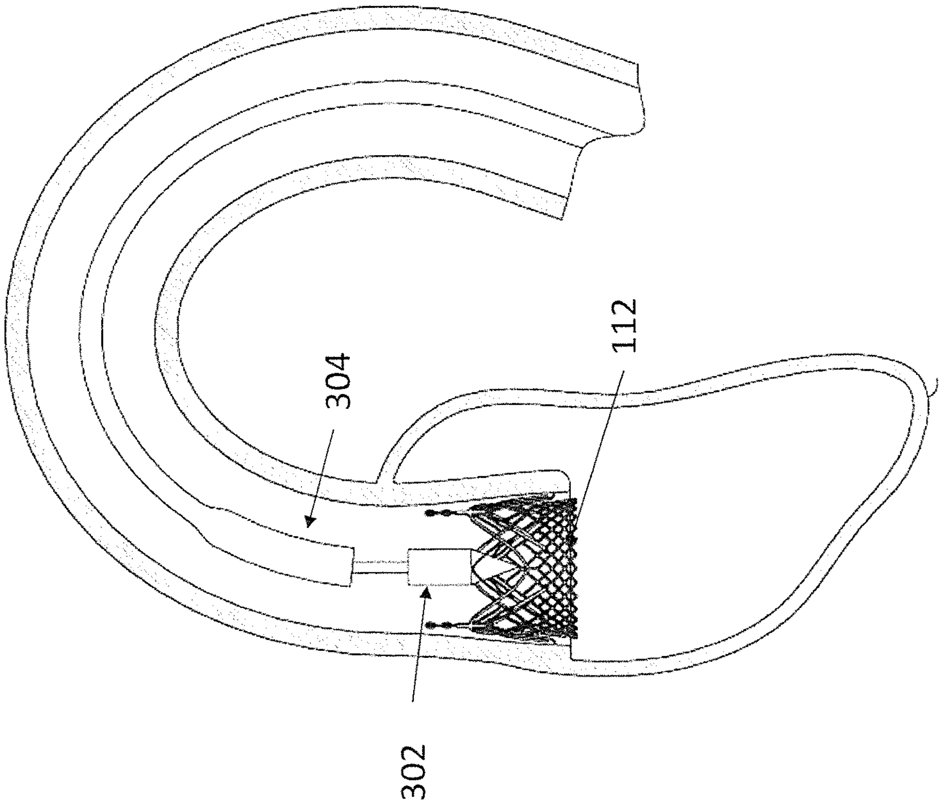
Figure 11E:
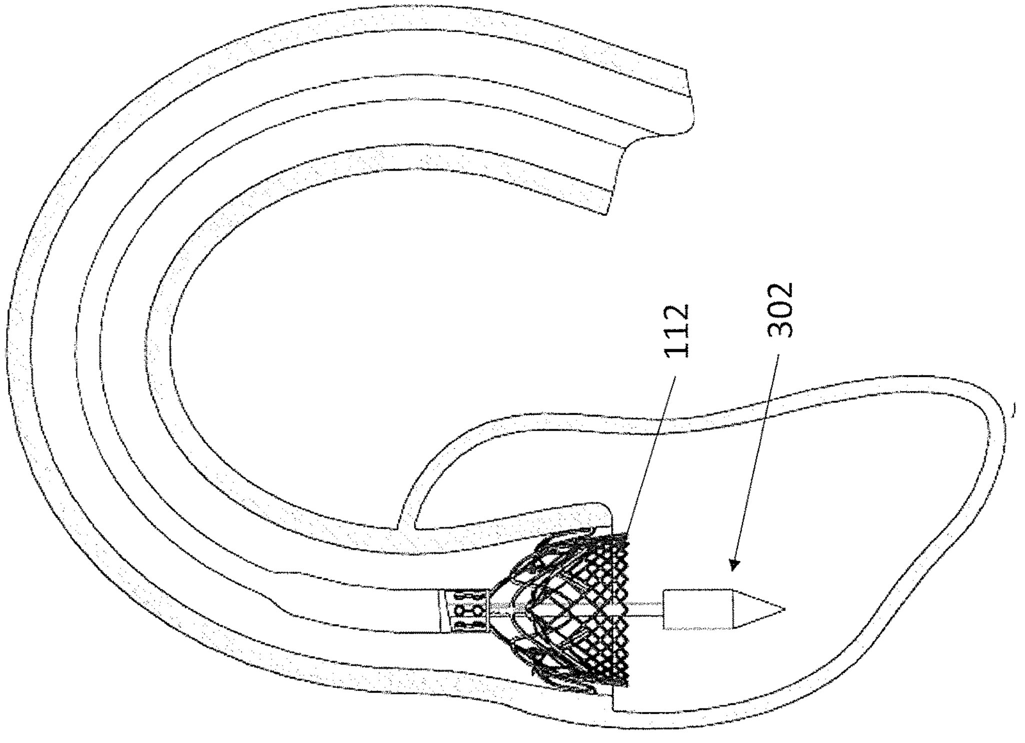
Figure 11G:
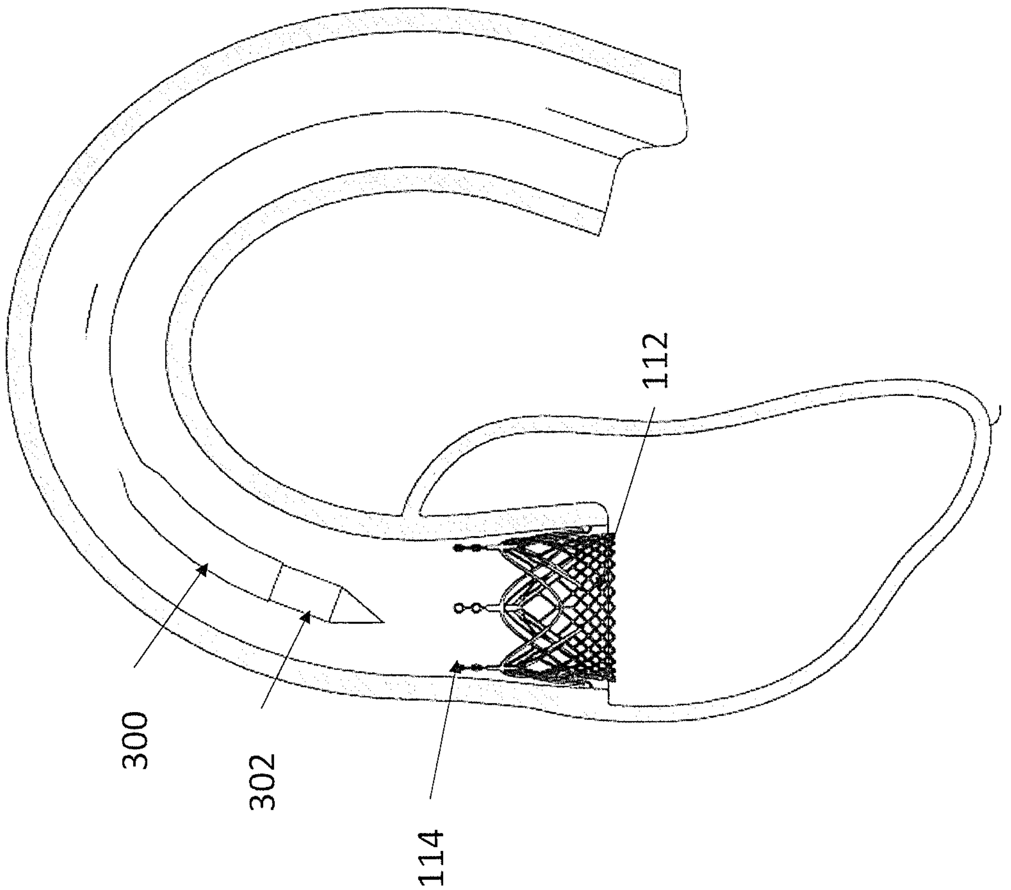

Referring to FIG. 11A, the catheter 300 with the device 100 retained therein is introduced via a puncture wound at upper thigh region through the femoral artery, and advanced through the aortic arch and the ascending aorta to the location of the aortic annulus 400, and a portion of the capsule passes through the aortic annulus into the ventricle. Next, in FIG. 11B, the proximal sheath 304 is retracted so that the distal (eyelet 172) ends of the clipping arms 164, 166 are exposed in the ventricle. In the next step (see FIG. 11C), the device 100 is retracted by retracting the delivery system 300 so that the distal (eyelet 172) ends of the clipping arms 164, 166 have cleared the aortic annulus and are now positioned inside the aortic root. With the distal ends of the clipping arms 172 positioned above the native aortic valve, the device 100 is advanced distally until the clipping arms 164, 166 drop into the cusps of the native leaflets. See FIG. 11D. Since there are three of each clipping arm 164, 166, there are a total of six clipping arms which allow the six clipping arms to be spaced-apart within the native leaflets in the aortic annulus. Next, the distal sheath 302 is advanced to expose the distal end of the device 100, so that the distal end of the device 100 can be deployed. This is shown in FIG. 11E where the body 112 of the frame 110 is being expanded. At this point, the device 100 is secured at the aortic annulus. The proximal sheath 304 is then further retracted to deploy the commissure regions 114. See FIG. 11F. Finally, the distal tip sheath 302 is retracted into the proximal tip sheath 304, and the entire delivery system 300 is withdrawn from the human body. See FIG. 11G.

The method steps described in connection with FIGS. 11A-11G provide an advantageous way to adjust the position of the body 112 of the frame 110. Specifically, the distal sheath 302 is provided to retain the body 112 in its compressed configuration while the clipping arms 164, 166 are being released and positioned inside the cusps of the native leaflets. After the clipping arms 164, 166 have been properly positioned, the clinician can then maneuver the frame 110 in its compressed configuration so that the body 112 can be accurately positioned in the aortic annulus before it is released. The bands 322, 324 can help the clinician during this positioning step.

Figure 13:
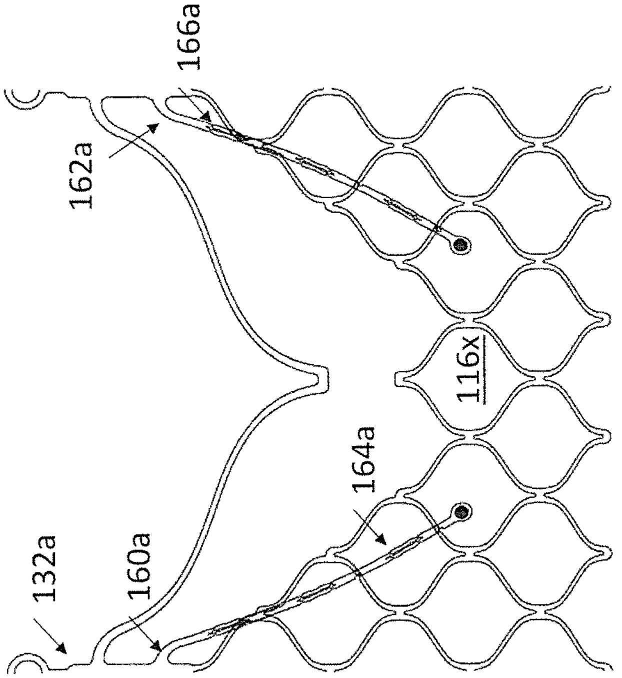
FIG. 13 is a flattened view of a portion of the frame of FIG. 12.
Figure 12:
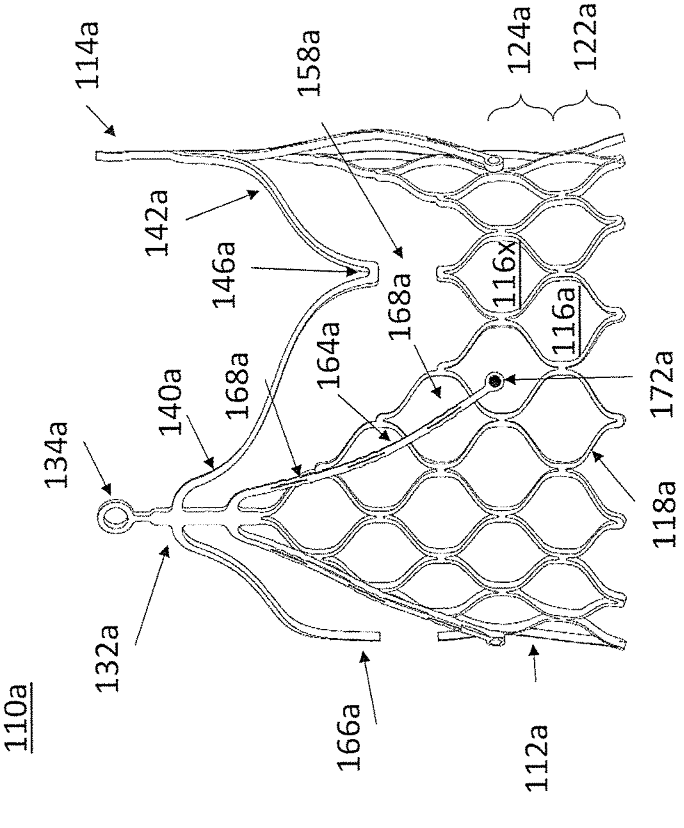
FIG. 12 is a side perspective view of the frame of a prosthetic heart valve device according to a second embodiment of the present invention.

FIGS. 12-13 illustrate a second embodiment for the frame 110 of the present invention. The frame 110*a* in FIGS. 12 and 13 is very similar to the frame 110 in FIGS. 1-9, so the same numerals used in FIGS. 1-9 will be used in FIG. 12 to designate the same elements except that an "a" is added to the numerals in FIG. 12. The frame 110*a* differs from the frame 110 in three ways.

First, the apex 146*a* is not connected to, or joined with, the cell 116*x* of the body 112*a*. Therefore, a space 158*a* (instead of the joint 158) is defined between the apex 146*a* and the apex of the cell 116*x* in row 124*a*. In other words, the first angled space 160 and the second angled space 162 mentioned in the first embodiment above are communicated with each other. Disconnecting the apex 146*a* and cell 116*x*, and creating a space 158*a*, allows the struts 140*a* and 142*a* of the leaflet backing to shape-set more naturally and reduces stress during shape-setting of the frame 110*a*.

Second, each clipping arm 164*a* and 166*a* can have more than one slot 168*a* that are spaced apart along the length of each clipping arm 164*a* and 166*a*. The inclusion of additional slots 168*a* allows for additional length to be obtained in the clipping arms 164*a*, 166*a*. The length of each clipping arm 164*a*, 166*a* is one factor determining the location of the tips 172*a* and thus, the placement of the device 100 in the native anatomy. In other words, by adding additional slots 168*a*, the length of each clipping arm 164*a*, 166*a* extends, thereby allowing the device 100 to sit higher in the native anatomy. Additionally, the clipping arms can be angled at a more obtuse angle to allow the tips 172*a* to sit closer to the inflow (distal) end of the frame 110. Reduction of the distance from the tips 172*a* to the inflow (distal) end of the frame 110 allows the device 100 to sit higher in the native anatomy, thus reducing the chance of conduction system disturbance, and thus PPI.

Third, only one eyelet 134*a* is provided at the commissure posts 132*a*, with the second eyelet 136 being omitted. The device 100 can be provided with a single or double eyelet, depending on the dock 310. A double-eyelet (134+136) configuration may provide a more secure locking with the dock 310 in the delivery system 300, while a single eyelet 134*a* will reduce the overall height of the device 100. Additionally, a double-eyelet configuration may provide a mechanism for additional modulation of the arm position in-vivo.

In addition, although the present invention illustrates the use of eyelets to clip the protrusions 320 inside the dock 310, other alternatives to the eyelets can be provided in the posts 132 to accomplish the same function. As one example, a key structure can be used.

Figure 14:
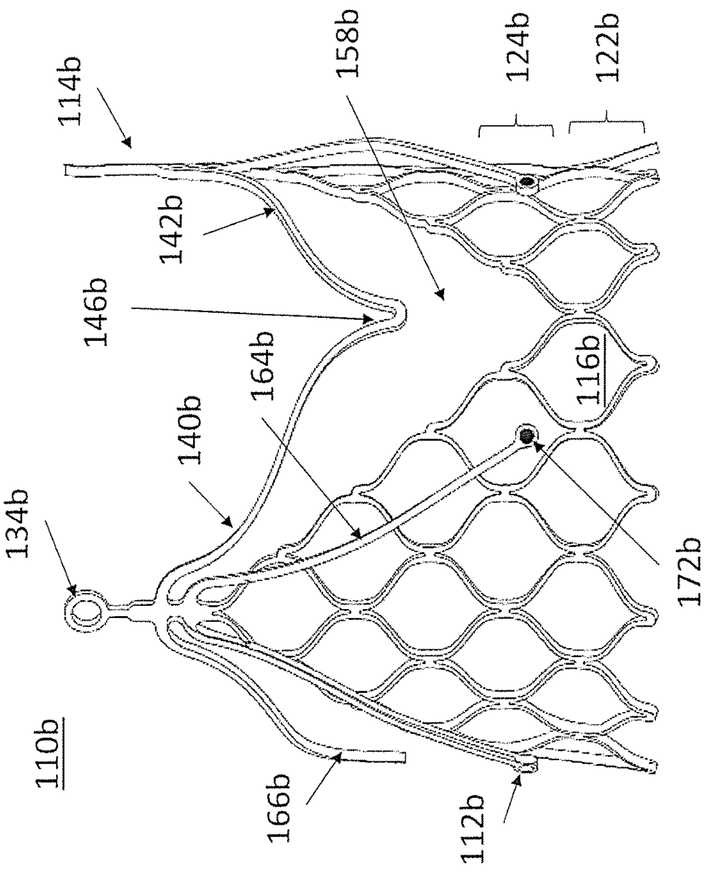
FIG. 14 is a side perspective view of the frame of a prosthetic heart valve device according to a third embodiment of the present invention.

FIG. 14 illustrates a third embodiment for the frame 110 of the present invention. The frame 110*b* in FIG. 14 is very similar to the frame 110*a* in FIGS. 12-13, so the same numerals used in FIGS. 12-13 will be used in FIG. 14 to designate the same elements except that a "b" is added to the numerals in FIG. 14. The frame 110*b* differs from the frame 110*a* primarily in that the cell 116*x* is completely omitted, and only the row of cells 116*b* at the distal-most inflow end continuously extends in a complete circle, so that the space or distance 158*b* is larger than the space 158*a*, and also the length of the arms 164*b* and 166*b* are slightly increased. Eliminating cell 116*x* allows for the additional beam length to be added to the frame 110. This additional beam length allows the device 100 to sit higher in the native anatomy, and reduce the risk of PPI. This can be seen in FIG. 14 where the position of the tip 172*b* is lower on the frame 110*b* when compared to the other embodiments.

Figure 15:
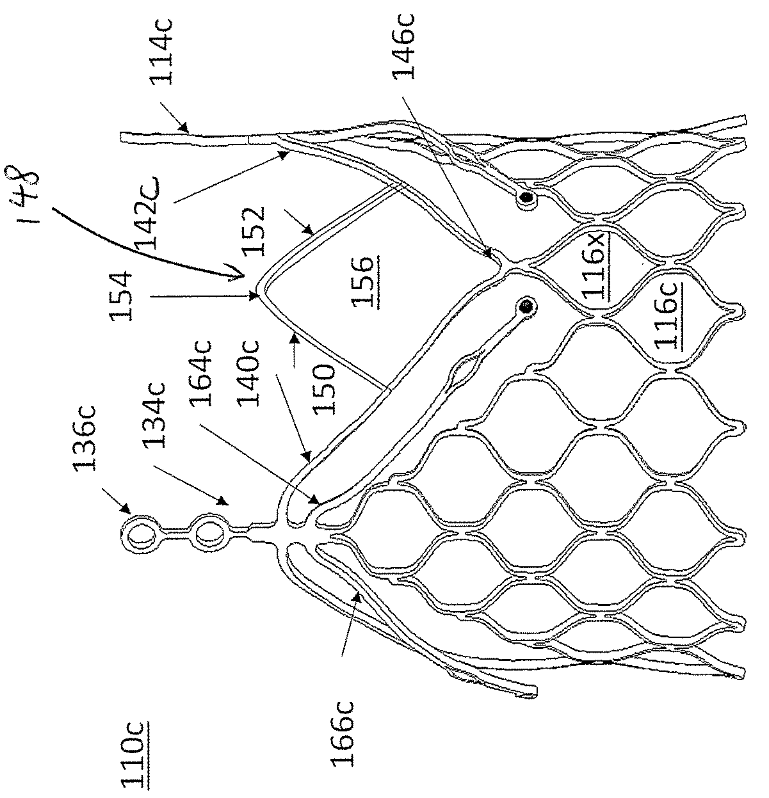
FIG. 15 is a side perspective view of the frame of a prosthetic heart valve device according to a fourth embodiment of the present invention.

FIG. 15 illustrates a fourth embodiment for the frame 110 of the present invention. The frame 110*c* in FIG. 15 is very similar to the frame 110 in FIGS. 1-9, so the same numerals used in FIGS. 1-9 will be used in FIG. 15 to designate the same elements except that a "c" is added to the numerals in FIG. 15. In this embodiment, a curved bridge 148 can connect each set of first and second arms 140*c* and 142*c* at about their midsections. Each bridge 148 has a first leg 150 extending from a first arm 140*c* and a second leg 152 extending from a second arm 142*c*, and the two legs 150 and 152 connect at a proximal-facing apex 154. Each set of first and second arms 140*c*, 142*c* and legs 150 and 152 define a generally diamond-shaped space 156. As an alternative of the curved bridge 148, a deformable meshed structure defined by an arrangement of cells can also be provided to connect each set of first and second arms 140*c* and 142*c* at about their midsections.

Figure 16:
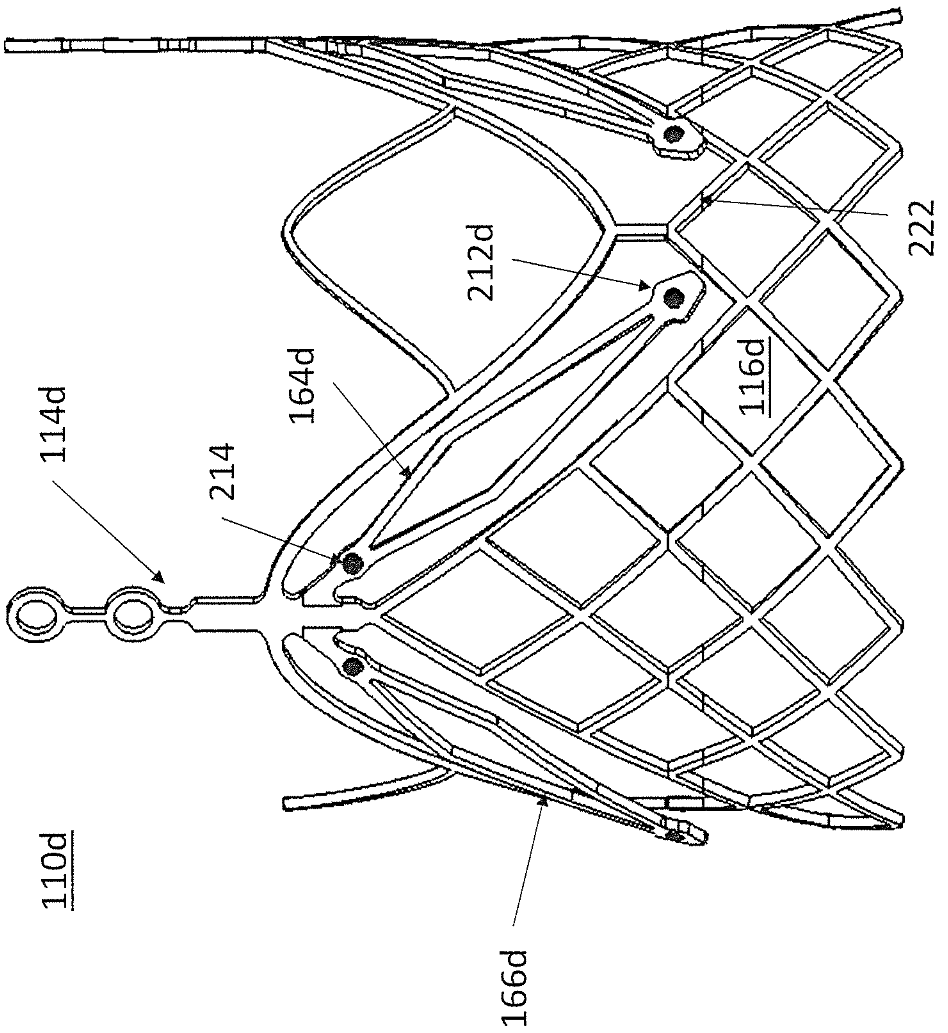
FIG. 16 is a side perspective view of the frame of a prosthetic heart valve device according to a fifth embodiment of the present invention.

FIG. 16. illustrates a fifth embodiment for the frame 110 of the present invention. The frame 110*d* in FIG. 16. is very similar to the frames 110 and 110*c* in FIGS. 1-9 and 15 so the same numerals used in FIGS. 1-9 and 15 will be used in FIG. 16 to designate the same elements except that a "d" is added to the numerals in FIG. 16. In this embodiment, an additional marker element is added to the connecting end of the clipping arms 164*d*, 166*d* (or to the two opposite ends of a respective clipping arm which has a hollowed structure extending along the length thereof). This allows for additional visibility under fluoroscopy in a clinical situation to better enable correct anatomical placement of the device. Based on the motion of the markers 212*d*, 214 during deployment, these two markers can assist in identifying which clipping arm 164*d*, 166*d* is behind the leaflet and which clipping arm is in front of the leaflet. For example, the marker that is moving at the rhythm of the heartbeat generally can help illustrate that it is touching the nadir of the native leaflets. By having radiopaque markers on the clipping arms and commissure regions 114*d*, the physician can easily ascertain that the clipping arms 164*d*, 166*d*, are located behind the native leaflets before full deployment of the device 100. This would make the procedure faster and safer.

Reviewing and comparing the embodiments in FIGS. 1 and 12-16 will illustrate an important aspect of the present invention in that the free ends (i.e., tips 172) of the clipping arms 164, 166 are positioned along a circumferential line (e.g., see 222 in FIG. 16) of the frame 110 which is closer to the inflow (distal) end of the frame 110 than to the outflow (proximal) end of the frame 110. The inflow end can be defined by the circumferential line defined by the distal-facing apices of the cells 116 in the first row 122, while the outflow end can be defined by circumferential line defined by the proximal-facing apices of the cells 116 in the fifth row 130.

As described in connection with FIG. 1, the distal (inflow) end of the body 112 can be flared to provide a mechanism for securing the frame 110 at the native annulus. FIGS. 17A, 17B, 18A and 18B illustrate two other embodiments that utilize different or additional mechanisms for securing the frame 110 at the native annulus.

Figure 17B:
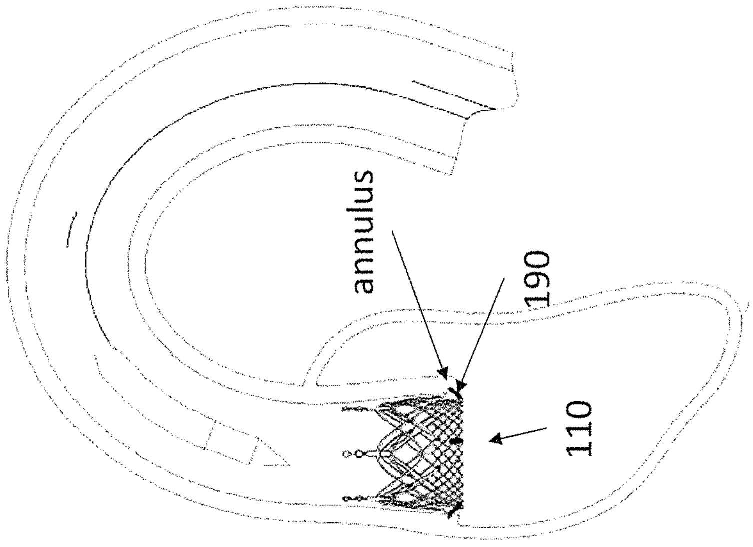
FIG. 17B illustrates the frame of FIG. 17A secured at a native annulus.
Figure 17A:
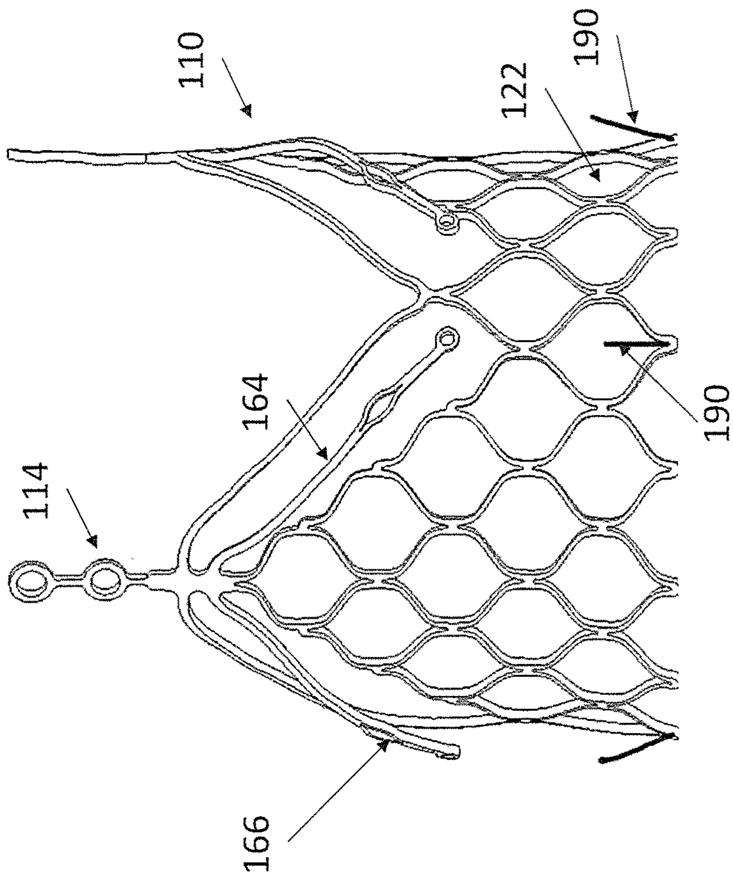
FIG. 17A illustrates a modification that can be made to the frame of FIG. 1.

FIG. 17A shows the same frame 110 as in FIG. 1, but with an everted strut 190 extending from the distal-most apex of some cells 116 in the row 122. These everted struts 190 can be shape-set to have one end connected to the distal-most apex of some cells 116 in the row 122, and an opposite free end which extends at an angle away from the body 112. FIG. 17B shows the location of the struts 110 when the frame 110 is secured at the native annulus.

Figure 18B:
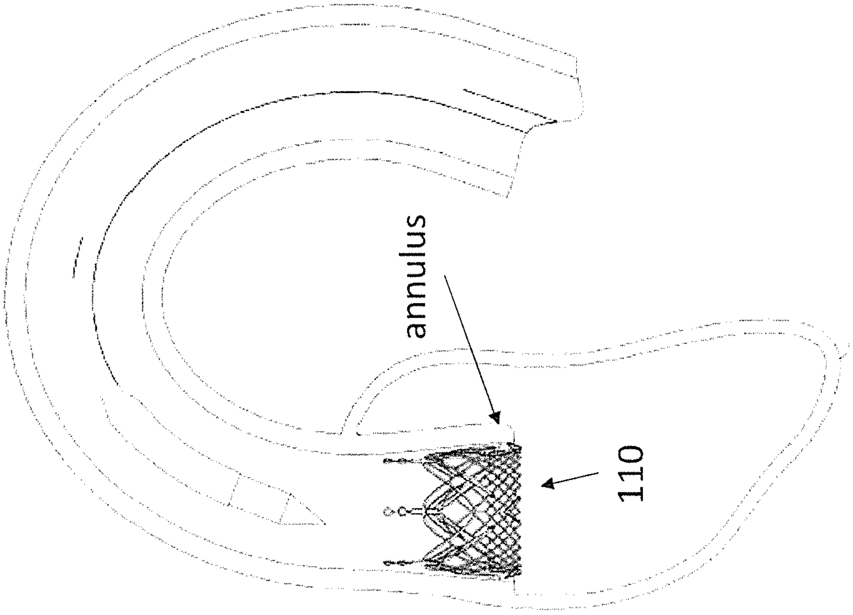
FIG. 18B illustrates the frame of FIG. 18A secured at a native annulus.
Figure 18A:
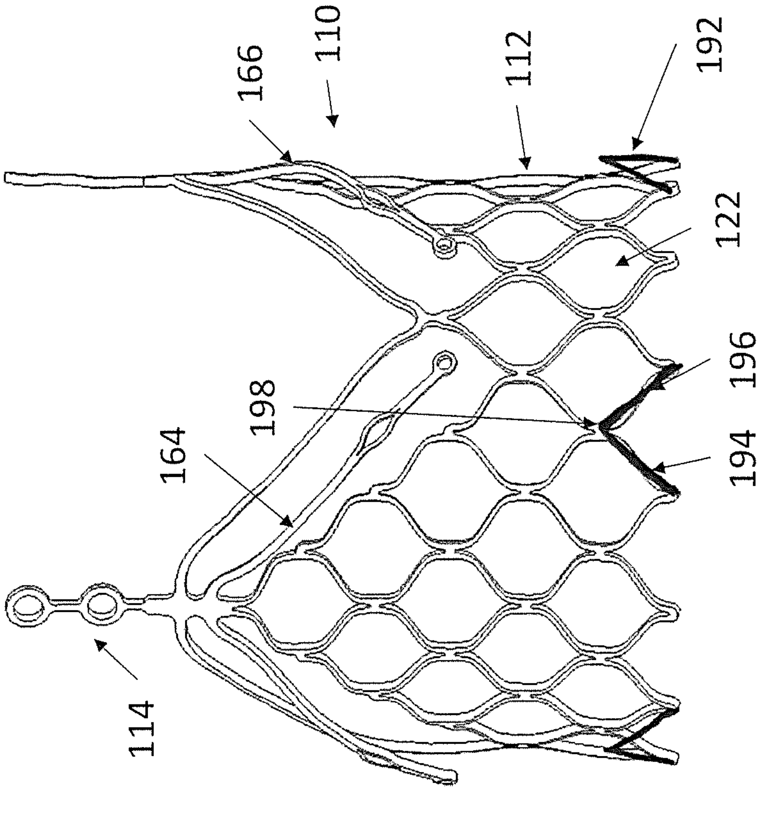
FIG. 18A illustrates another modification that can be made to the frame of FIG. 1.

FIG. 17B shows the same frame 110 as in FIG. 1, but with an everted cell 192 extending from the distal-most apex of a selected plurality of cells 116 in the row 122. Each everted cell 192 has two struts 194 and 196 that are connected to form an everted apex 198. These everted cells 192 can be shape-set to have one end of each strut 194, 196 connected to adjacent distal-most apices of some cells 116 in the row 122, and the opposite everted apex 198 extends at an angle away from the body 112. The cells 192 can even formed by removing certain cells 116 from the distal-most row 120 of cells. FIG. 18B shows the location of the cells 192 when the frame 110 is secured at the native annulus.

The dimensions and locations of the everted strut 190 and the everted cell 192 can be adjusted depending on the desired application. For example, the lengths of the struts 190, 194, 196 can be varied, and these struts 190, 194, 196 can even be curved. As another example, an everted strut 190 can be provided on any number of apices, or in any arrangement. For example, everted struts 190 can be provided on alternating apices. Also, the struts 194, 196 of the everted cells 192 do not need to extend from adjacent apices, but can extend from two separate apices that are separated by one apex.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A prosthetic heart valve device, comprising:

a frame that is defined by an annular body that is defined by an arrangement of cells, the body having a distal inflow end, and a proximal outflow end, the frame further having:

three spaced-apart connection portions;

a first clipping arm and a second clipping arm that extend from opposite sides of each connection portion, and each clipping arm having a free end with a tip provided at the free end, and a slot that defines an open space prior to shape-setting and which is closed after shape-setting;

wherein the body has a first diameter at a circumferential line location where the tips of the clipping arms are located, and the tips of the clipping arms extend away from the body and define a circumferential line with a second diameter, with the second diameter being greater than the first diameter; and a leaflet assembly having a plurality of leaflets that are secured to the frame.

2. The device of claim 1, wherein the slot in each clipping arm is a first slot, and wherein each clipping arm further includes a second slot that is spaced apart from the first slot.

3. The device of claim 1, wherein the frame has three spaced-apart commissure regions, and wherein the connection portion is configured as a commissure post of the respective commissure region extending from the proximal outflow end.

4. The device of claim 3, wherein each clipping arm extends from each commissure post at an obtuse angle with respect to each commissure post.

5. The device of claim 3, wherein the frame further includes a first frame arm and a second frame arm that extend from opposite sides of each commissure post, with the first frame arm from one commissure post is connected at a distal-facing apex with the second frame arm from an adjacent commissure post.

6. The device of claim 5, wherein the first clipping arm and second clipping arm extend from opposite sides of each commissure post from a location between the first frame arm and the second frame arm, respectively.

7. The device of claim 5, wherein each distal-facing apex is connected at a joint with an apex of a cell in the body.

8. The device of claim 1, wherein a radiopaque marker is provided at the tip of each clipping arm.

9. The device of claim 5, wherein a bridge connects each set of first and second frame arms from adjacent commissure posts.

10. The device of claim 3, wherein each commissure post has at least one eyelet.

11. The device of claim 3, wherein a radiopaque marker is provided at a location where each clipping arm is connected to a commissure post.

12. The device of claim 1, wherein the body has a plurality of rows of cells, with the number of cells in each row of cells decreasing from the distal inflow end towards the proximal outflow end.

13. The device of claim 1, wherein the body is flared so that the distal inflow end has a larger diameter than the remainder of the body.

14. The device of claim 1, further including a securement mechanism provided at the distal inflow end of the body.

* * * * *